US008631831B2

(12) United States Patent
Dimalanta, Jr. et al.

(10) Patent No.: US 8,631,831 B2
(45) Date of Patent: Jan. 21, 2014

(54) MULTI-COMPLIANT TUBING

(75) Inventors: Ramon Carsola Dimalanta, Jr., Trabuco Canyon, CA (US); Grace Chuang Liao, Irvine, CA (US); Robert Harry Peterson, Rancho Santa Margarita, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 716 days.

(21) Appl. No.: 12/540,014

(22) Filed: Aug. 12, 2009

(65) Prior Publication Data

US 2010/0056991 A1     Mar. 4, 2010

Related U.S. Application Data

(63) Continuation-in-part of application No. 12/204,284, filed on Sep. 4, 2008.

(51) Int. Cl.
*F16L 11/00* (2006.01)
(52) U.S. Cl.
USPC ............. 138/116; 138/119; 138/120; 604/35; 604/118; 604/174
(58) Field of Classification Search
USPC .................... 138/116, 119, 120; 604/35, 118, 604/174–180
See application file for complete search history.

(56) References Cited

U.S. PATENT DOCUMENTS

| 3,336,764 A | 8/1967 | Chambers |
| 3,589,363 A | 6/1971 | Banko |
| 3,994,297 A | 11/1976 | Kopf |
| 3,997,097 A | 12/1976 | Embury |
| 4,223,676 A | 9/1980 | Wuchinich |
| 4,246,902 A | 1/1981 | Martinez |
| 4,493,694 A | 1/1985 | Wuchinich |
| 4,515,583 A | 5/1985 | Sorich |

(Continued)

FOREIGN PATENT DOCUMENTS

| DE | 3942192 | 6/1991 |
| DE | 10233053 A1 | 2/2004 |

(Continued)

OTHER PUBLICATIONS

International Searching Authority, Written Opinion of the International Searching Authority, PCT/US09/055415, Mar. 4, 2011, 6 pages.

(Continued)

*Primary Examiner* — James Hook (57) ABSTRACT

In various embodiments, aspiration tubing connecting a handpiece to a surgical console may include a high compliant section, a transition section, and a low compliant section. In some embodiments, the high compliant section may have a lower durometer and/or different geometry than the low compliant section. The transition section may take a number of forms, including a connector or a continuous section of tubing that gradually increases in durometer and/or changes geometry through the length of the tubing. In the various embodiments, the high compliant section may provide flexibility near the handpiece to make the handpiece easier to hold and maneuver while the low compliant section may reduce the effects of occlusion break surge. In some embodiments, the high compliant section may include, for example, ribs, stiffening rings, a stiffening sleeve, or a stiffening sock to increase the stiffness of the high compliant section.

17 Claims, 11 Drawing Sheets

(56) References Cited

U.S. PATENT DOCUMENTS

| | | |
|---|---|---|
| 4,553,957 A | 11/1985 | Williams et al. |
| 4,589,415 A | 5/1986 | Haaga |
| 4,609,368 A | 9/1986 | Dotson, Jr. |
| 4,627,844 A | 12/1986 | Schmitt |
| 4,662,404 A | 5/1987 | LeVeen et al. |
| 4,750,902 A | 6/1988 | Wuchinich et al. |
| 4,816,018 A | 3/1989 | Parisi |
| 4,869,715 A | 9/1989 | Sherburne |
| 4,922,902 A | 5/1990 | Wuchinich |
| 4,954,055 A | 9/1990 | Raible et al. |
| 4,989,583 A | 2/1991 | Hood |
| 5,154,694 A | 10/1992 | Kelman |
| 5,242,385 A | 9/1993 | Strukel |
| 5,261,885 A | 11/1993 | Lui |
| 5,305,799 A * | 4/1994 | Dal Palu ............ 138/109 |
| 5,318,515 A | 6/1994 | Wilk |
| 5,340,330 A | 8/1994 | Dolson et al. |
| 5,358,493 A * | 10/1994 | Schweich et al. ............ 604/264 |
| 5,359,996 A | 11/1994 | Hood |
| 5,399,160 A | 3/1995 | Dunberger et al. |
| 5,476,448 A | 12/1995 | Urich |
| 5,533,878 A | 7/1996 | Iwata |
| 5,549,547 A | 8/1996 | Cohen et al. |
| 5,560,398 A | 10/1996 | Pfleger |
| 5,568,944 A | 10/1996 | Kawasaki |
| 5,616,120 A | 4/1997 | Andrews et al. |
| 5,653,265 A | 8/1997 | Nakagawa et al. |
| 5,662,144 A | 9/1997 | Lo et al. |
| 5,685,841 A | 11/1997 | Mackool |
| 5,700,240 A | 12/1997 | Barwick et al. |
| 5,704,401 A | 1/1998 | Fukui et al. |
| 5,873,851 A | 2/1999 | Nilsson |
| 5,897,537 A | 4/1999 | Berg et al. |
| 5,947,953 A * | 9/1999 | Ash et al. ............ 604/508 |
| 5,988,700 A | 11/1999 | Prichard |
| 6,050,971 A | 4/2000 | Garnier et al. |
| 6,119,731 A | 9/2000 | Nakagawa et al. |
| 6,159,175 A | 12/2000 | Strukel et al. |
| 6,283,974 B1 | 9/2001 | Alexander |
| 6,319,454 B1 * | 11/2001 | Nakagawa et al. ............ 264/515 |
| 6,579,259 B2 | 6/2003 | Stevens et al. |
| 6,599,271 B1 | 7/2003 | Easley |
| 6,629,948 B2 | 10/2003 | Rockley et al. |
| 6,878,142 B2 | 4/2005 | Lawrence et al. |
| 6,913,041 B2 | 7/2005 | Lehnhardt et al. |
| 6,960,182 B2 | 11/2005 | Moutafis et al. |
| 7,172,578 B2 | 2/2007 | Mackool |
| 7,371,224 B2 | 5/2008 | Haischmann et al. |
| 7,484,769 B2 | 2/2009 | Domash et al. |
| 7,806,889 B2 * | 10/2010 | Raulerson et al. ............ 604/523 |
| 2002/0055725 A1 | 5/2002 | Verkaart et al. |
| 2002/0128560 A1 | 9/2002 | Urich |
| 2003/0195460 A1 | 10/2003 | Kadziauskas |
| 2004/0034333 A1 | 2/2004 | Seese et al. |
| 2004/0039351 A1 * | 2/2004 | Barrett ............ 604/272 |
| 2004/0116901 A1 | 6/2004 | Appling |
| 2005/0070859 A1 | 3/2005 | Cull et al. |
| 2005/0080375 A1 | 4/2005 | Kadziauskas et al. |
| 2005/0096585 A1 * | 5/2005 | Schon et al. ............ 604/43 |
| 2005/0135974 A1 | 6/2005 | Harvey et al. |
| 2006/0041220 A1 | 2/2006 | Boukhny et al. |
| 2006/0084937 A1 | 4/2006 | Akahoshi |
| 2006/0135974 A1 | 6/2006 | Perkins |
| 2006/0161101 A1 | 7/2006 | Dimalanta et al. |
| 2006/0173404 A1 | 8/2006 | Urich |
| 2006/0224163 A1 | 10/2006 | Sutton |
| 2006/0253062 A1 | 11/2006 | Liao et al. |
| 2006/0293646 A1 | 12/2006 | Whayne et al. |
| 2007/0032777 A1 | 2/2007 | Perkins et al. |
| 2007/0043338 A1 | 2/2007 | Moll et al. |
| 2007/0043351 A1 | 2/2007 | Fleischman et al. |
| 2007/0078440 A1 | 4/2007 | Perkins et al. |
| 2007/0098578 A1 | 5/2007 | Morgan |
| 2007/0100285 A1 * | 5/2007 | Griffin et al. ............ 604/164.11 |
| 2007/0149919 A1 | 6/2007 | Perkins et al. |
| 2007/0149950 A1 | 6/2007 | Perkins et al. |
| 2007/0250040 A1 | 10/2007 | Provost et al. |
| 2007/0267012 A1 | 11/2007 | McCarthy |
| 2008/0125699 A1 | 5/2008 | Davis et al. |
| 2008/0300539 A1 | 12/2008 | Vreeman et al. |
| 2010/0057092 A1 | 3/2010 | Peterson |

FOREIGN PATENT DOCUMENTS

| | | |
|---|---|---|
| DE | 10233053 B4 | 2/2005 |
| EP | 0937481 A1 | 8/1999 |
| EP | 1716828 A1 | 11/2006 |
| EP | 1716828 B1 | 5/2008 |
| EP | 1917987 A2 | 5/2008 |
| EP | 1917987 A3 | 8/2008 |
| EP | 1917987 B1 | 12/2009 |
| EP | 2161046 A1 | 3/2010 |
| FR | 964069 | 8/1950 |
| JP | 05-305096 A | 11/1993 |
| JP | 10-071166 A | 3/1998 |
| JP | 10071166 A | 3/1998 |
| WO | WO 98/007398 A1 | 2/1998 |
| WO | WO 99/038549 A1 | 8/1999 |
| WO | WO 2006/069016 A1 | 6/2006 |
| WO | WO 2010/027619 A2 | 3/2010 |
| WO | WO 2010/027924 A2 | 3/2010 |
| WO | WO 2010/027619 A3 | 4/2010 |
| WO | WO 2010/027924 A3 | 4/2010 |

OTHER PUBLICATIONS

International Searching Authority, International Preliminary Report on Patentability, PCT/US09/055415, Mar. 8, 2011, 7 pages.

Peterson, Robert, Varying Material Properties of a Single Fluidic Line in Ophthalmology Tubing, U.S. Appl. No. 12/204,284, filed Aug. 27, 2009, 14 pages.

Kishimoto, Makoto, MD, OPESAVER—Super Irrigation System, Techniques in Ophthalmology, Mar. 2006, 6 pages, vol. 4, Issue 1, Lippincott Williams & Wilkins, Shiga, Japan.

Hook, James F., Final Office Action, U.S. Appl. No. 12/204,284, Mar. 31, 2011, and Response (Notice of Appeal) filed Jun. 27, 2011, 26 pages.

European Patent Office, European Search Report, European Paten Application No. EP 09 17 5773.2, Jan. 28, 2010, 5 pages.

International Searching Authority, Written Opinion of the International Searching Authority, PCT/US09/053708, Mar. 15, 2010, 6 pages.

Prosecution History of U.S. Appl. No. 11/591,960, filed Nov. 2, 2006, 510 pages.

Dr. Ulrich Naumann, Notice of Opposition and EPO Communication, Sep. 23, 2010, 25 pages.

Wolgang Ruchert, Contribution to the Development of an Elastic Lens with a Variable Focal Length for Use in an Artificial Accommodation System.

Prosecution History of U.S. Appl. No. 11/591,980, filed Nov. 2, 2006, 471 pages.

Publication No. 2010/0057092, Office Action Mailed Oct. 7, 2010 and Response filed Jan. 2, 2011, 31 pages.

* cited by examiner

MULTI-COMPLIANT TUBING

PRIORITY CLAIM

This application is a continuation-in-part application of U.S. patent application Ser. No. 12/204,284 titled "Varying Material Properties of a Single Fluidic Line in Ophthalmology Tubing" which was filed Sep. 4, 2008 whose inventor is Robert H. Peterson which is hereby incorporated by reference in its entirety as though fully and completely set forth herein.

FIELD OF THE INVENTION

The present invention generally pertains to ophthalmic surgery. More particularly, but not by way of limitation, the present invention pertains to tubing for ophthalmic surgery.

DESCRIPTION OF THE RELATED ART

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an intraocular lens (IOL).

Cataractous lenses may be removed by a surgical technique called phacoemulsification. The diseased lens, once removed, may be replaced by an artificial lens. During procedure to remove the lens, a cutting tip on a phacoemulsification handpiece may be inserted into the diseased lens and vibrated ultrasonically. The vibrating cutting tip may liquefy or emulsify the lens so that the lens may be aspirated out of the eye. The material may be aspirated out of the eye through an aspiration port on the end of the phacoemulsification handpiece. Irrigation may also be provided at the end of the phacoemulsification handpiece to assist in removal of the lens material. A dangerous condition can occur if lens material temporarily clogs the aspiration port (or attached aspiration line). During the clog, the vacuum in the aspiration line may build, and when the lens material finally breaks free, the excess vacuum pressure (an occlusion break surge) may then aspirate portions of the eye which may cause damage to the eye (e.g., collapse). To reduce the effect of the excess vacuum pressure, aspiration tubing may be made of a high durometer material. However, high durometer material is often difficult to handle as the material is usually not very flexible.

SUMMARY OF THE INVENTION

In various embodiments, sterilized tubing for use with a fluidics cassette and a handpiece of an ophthalmologic system may be provided. The ophthalmologic system may be a phacoemulsification, liquefaction, or other type of surgical system utilizing irrigation/aspiration handpieces. In various embodiments, tubing (e.g., aspiration tubing and/or irrigation tubing) connecting a handpiece to a surgical console may include a high compliant section, a transition section, and a low compliant section. In some embodiments, the high compliant section may have a lower durometer and/or a different geometry than the low compliant section. The transition section may take a number of forms, including a connector or a continuous section of tubing that gradually increases in durometer and/or changes in geometry through the length of the tubing.

In the various embodiments, the high compliant section may provide flexibility near the handpiece to make the handpiece easier to hold and maneuver while the low compliant section may reduce the effects of occlusion break surge. In some embodiments, the high compliant section may include, for example, ribs, stiffening rings, a stiffening sleeve, or a stiffening sock to increase the stiffness of the high compliant section.

In some embodiments, twin bore ophthalmologic tubing may be used. The twin bore ophthalmologic tubing may include a first tube and a second tube (e.g., one tube for irrigation and one tube for aspiration) joined along substantially the length of the twin bore ophthalmologic tubing. The tubes may have ends adapted for connection to the fluidics cassette and to the handpiece. The second tube may have two portions of differing hardness with one of the portions being at one of the ends of the second tube. In some embodiments, the first portion may be about 6" to about 12" long and may have a hardness of about 60 shore A to about 70 shore A while the other portion may have a hardness of about 80 shore A to about 90 shore A (other hardness values and lengths are also contemplated). In various embodiments, the second tube may have another portion at the other end of the second tube with about the same hardness as the first end portion. In some embodiments, the first tube may have portions of differing hardness. Portions of the first and the second tubes may have about the same hardness which corresponds to each other along a portion of the twin bore ophthalmologic tubing.

Embodiments provide tubing with low compliance and low resistance to movement of the tubing (even when connected to surgical handpieces and fluidics cassettes). Embodiments provide tubing with rapid vacuum rise times and good occlusion break response in the aspiration line of the tubing. Tubing of embodiments are provided which allow characteristics such as compliance, navigability, occlusion break response, and vacuum rise time to be controlled by selecting hardness levels for various portions of the tubing.

BRIEF DESCRIPTION OF THE DRAWINGS

For a more complete understanding of the present invention, reference is made to the following description taken in conjunction with the accompanying drawings in which.

DETAILED DESCRIPTION OF THE EMBODIMENTS

It is to be understood that both the foregoing general description and the following detailed description are exemplary and explanatory only and are intended to provide a further explanation of the present invention as claimed.

Figure 1:
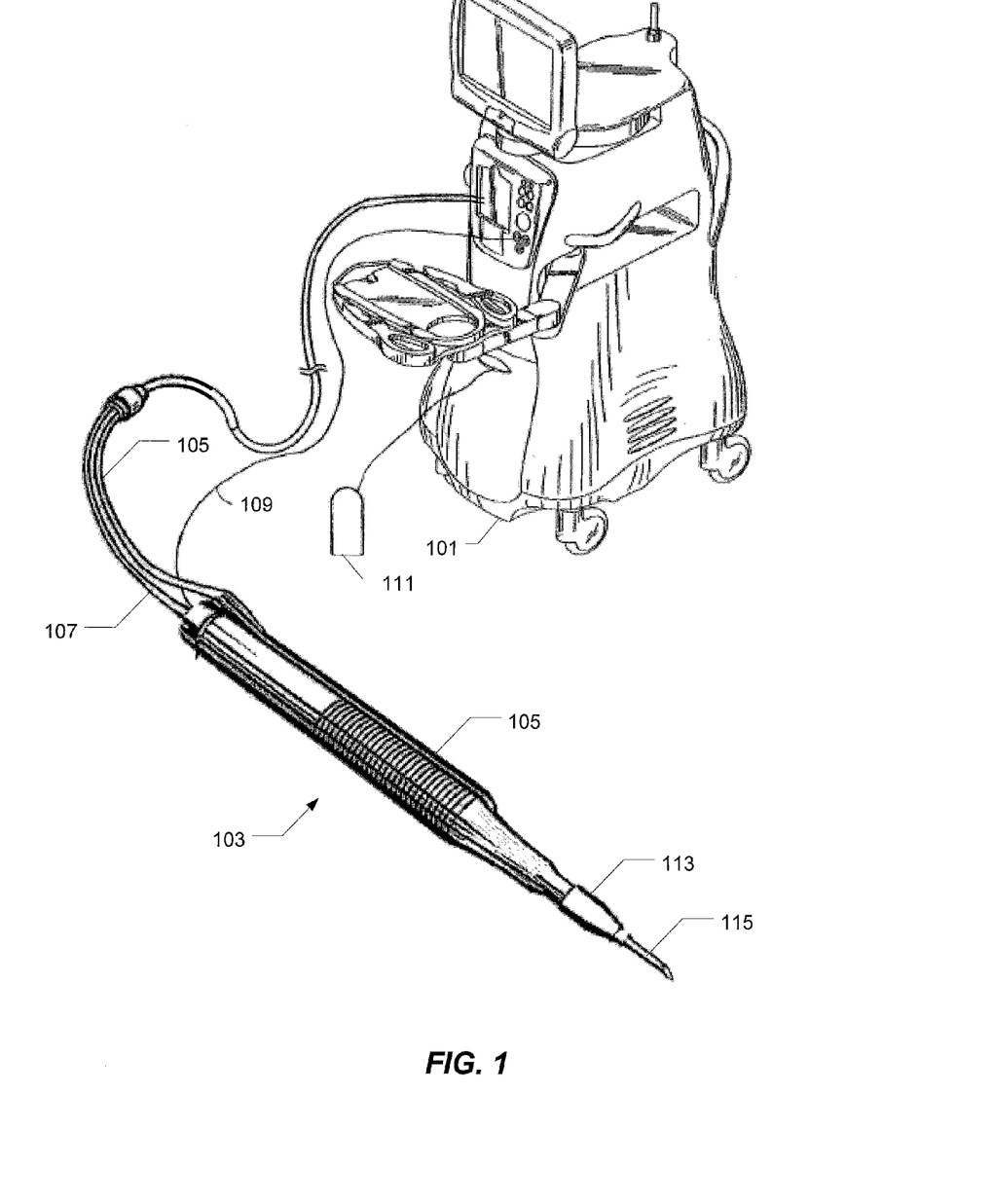
FIG. 1 illustrates a phacoemulsification surgical console connected to a handpiece through an irrigation line and an aspiration line, according to an embodiment.

FIG. 1 illustrates a phacoemulsification surgical console 101 connected to a handpiece 103 through an irrigation line 105 and an aspiration line 107. In some embodiments, power may be supplied to handpiece 103 through electrical cable 109 and flow through lines 105 and 107 may be controlled by a user (e.g., via footswitch 111) to perform a phacoemulsification procedure. Console 101 may contain appropriate hardware and software for providing control signals to handpiece 103. In some embodiments, irrigation may be delivered through the tip at an irrigation sleeve 113 at least partially surrounding a cutting tip 115. One example of a handpiece for a phacoemulsification procedure is described in U.S. Patent Application Publication entitled "Ultrasound Handpiece," Publication No. 2006/0041220, Ser. No. 11/183,591, by Mikhail Boukhny, James Y. Chon, and Ahmad Salehi filed Jul. 18, 2005, which is hereby incorporated by reference in its entirety as though fully and completely set forth herein.

As surgical personnel operate on patient 842 (see FIG. 8) using handpiece 103 to perform certain delicate techniques (e.g., phacoemulsification, liquefaction or other methods of extraction of cataracts), irrigation fluid may flow from fluidics module 843 through irrigation tube 105 and into handpiece 103. Within handpiece 103, a liquefaction pulse engine may generate pulses of warmed irrigation fluid which surgical personnel may direct at targeted tissues using handpiece 103 (in some embodiments, a pulse engine may not be used). Vacuum applied to the aspiration line 107 may cause aspiration of the irrigation fluid (and tissues removed therewith) from patient 842 via aspiration line 107. The irrigation fluid, under the influence of the vacuum, may flow from handpiece 103, through aspiration line 107, and into fluidics module 843. As the fluidics module 843 aspirates out the tissue from the patient 842, through the handpiece, pressure variations may develop as a results of occlusion or partial occlusion of the distal end of the handpiece. It may be desired to avoid these pressure variations.

In some embodiments, aspiration tube 107 may comply with variations in the pressure therein as surgical personnel utilize handpiece 103 to extract and aspirate tissues from patient 842. In some embodiments, aspiration tube 107 may be of sufficient hardness to prevent, or limit, compliance of aspiration tube 107 with the vacuum pressure which might be therein. Thus, at least some aspects of ophthalmologic surgery may call for aspiration tubes 107 made from materials having relatively high hardness. Aspiration tubes 107 having relatively high hardness may be provided by some embodiments which exhibit little or no compliance. Aspiration tubes 107 may therefore store little or no energy during occlusions. Irrigation tubes 105 may also exhibit little or no compliance in some embodiments although compliance of irrigation tubes 105 may not be a factor in some situations.

Compliance levels (and thereby stiffness) of irrigation tube 105 and aspiration tube 107 may create reaction forces, moments, torques, etc. in irrigation tube 105 and aspiration tube 107, respectively. Such reactions may interfere with potentially delicate techniques which surgical personnel may be performing with handpiece 103. Surgery can therefore be complicated by compliance of irrigation tube 105, aspiration tube 107, or both. Thus, at least one aspect of ophthalmologic surgery (for instance, navigability of handpiece 103) may call for irrigation tubes 105 and aspiration tubes 107 made from materials having relatively low compliance and thereby more flexible. Other aspects of ophthalmologic surgery besides navigability (for instance, compliance of irrigation tube 105 and aspiration tube 107) may call for irrigation tubes 105 and aspiration tubes 107 made from materials having relatively high compliance. Thus, maneuverability may call for tubes of relatively high compliance while navigability may call for tubes of relatively low compliance.

Figure 2:
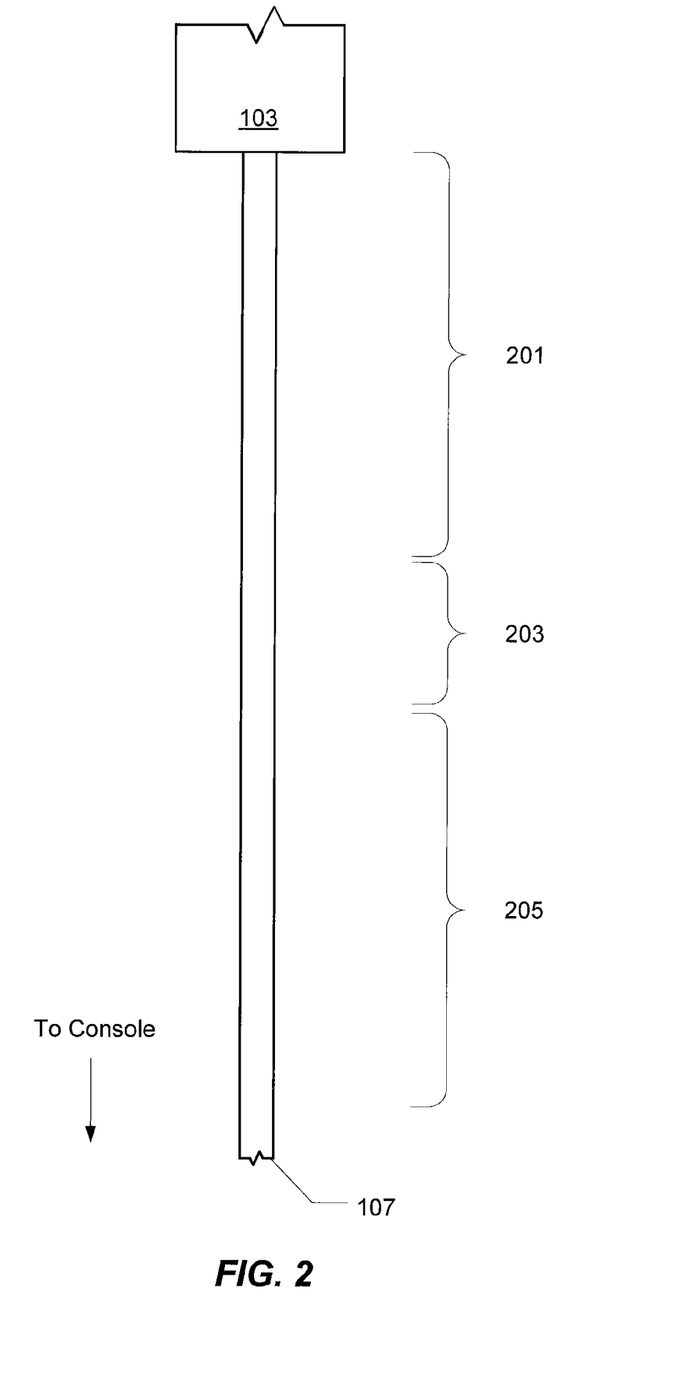
FIG. 2 illustrates a diagram of an aspiration line, according to an embodiment.

FIG. 2 illustrates aspiration tubing 107 connected to a handpiece 103, according to an embodiment. Aspiration tubing 107 connected to the handpiece 103 may include a high compliant section 201, a transition section 203, and a low compliant section 205. In the various embodiments, the high compliant section 201 may provide flexibility near the handpiece 103 to make the handpiece 103 easier to hold and maneuver while the low compliant section 205 may reduce the effects of occlusion break surge. The high compliant section 201 may have a lower durometer (and therefore be more flexible) than the low compliant section 205. In some embodiments, the high compliant section 201 may have a similar durometer as the low compliant section 205, but may include a different geometry than the low compliant section 205 to allow the high compliant section 201 to be more flexible than the low compliant section 205. The different geometry for the high compliant section 201 may include a thinner tubing wall (thinner than the low compliant section 205) through all or a portion of a cross section of the high compliant section 201. For example, the geometry may include slits or other reduced material cross sections. Several possible geometries for the high compliant section 201 are shown in the cross sectional views of FIGS. 5a-e. Other geometries for the high compliant section 201 are also contemplated. In some embodiments, the high compliant section 201 may have lower durometer and a different geometry than the low compliant section 205.

In some embodiments, the low compliant section 205 may be less flexible than the high compliant section 201 because the low compliant section 205 may have a higher durometer and/or a different geometry than the high compliant section 201. The different geometry for the low compliant section 205 may include a thicker tubing wall (thicker than the high compliant section 201) through all or a portion of a cross section of the low compliant section 205. The geometries may include protrusions or other increased material cross sections. Several possible geometries for the low compliant section 205 are shown in the cross sectional views of FIGS. 6a-f. Other geometries for the low compliant section 205 are also contemplated.

Figure 3A:
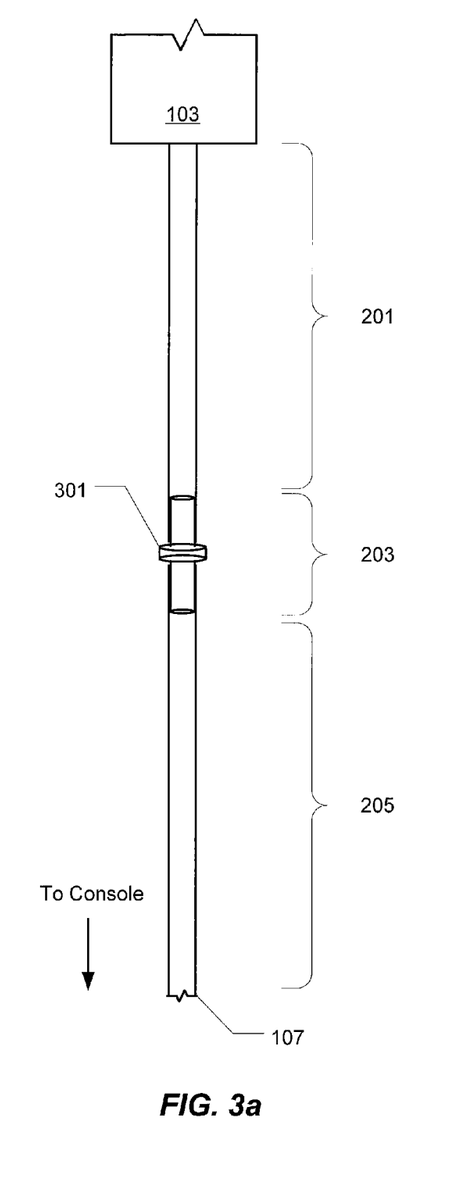
FIGS. 3a-c illustrate embodiments of the transition section.
Figure 3B:
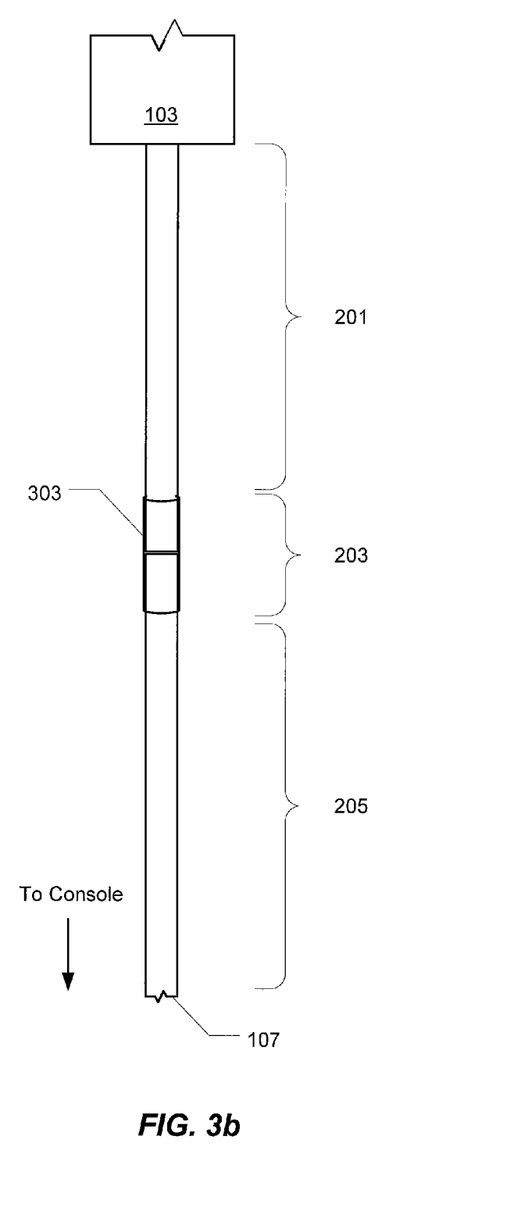
Figure 3C:
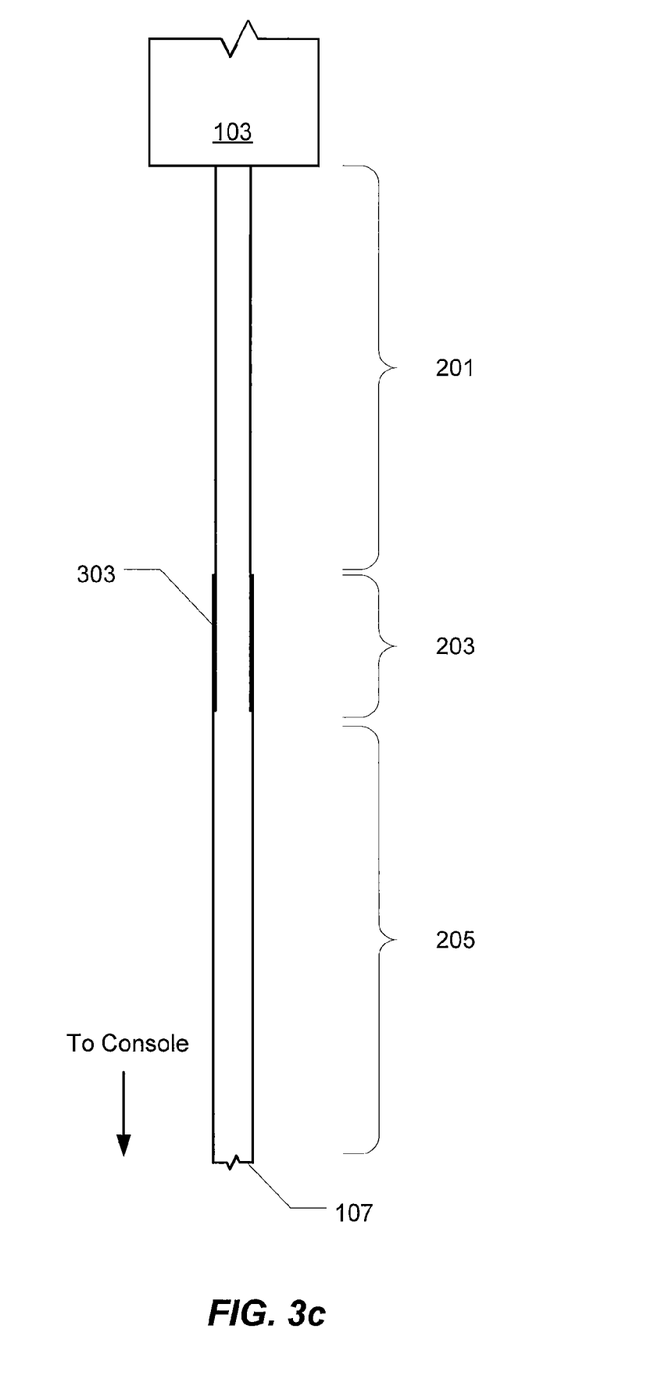

In various embodiments, the transition section 203 may take a number of forms. For example, in some embodiments, the transition section 203 may include a connector 301 (see FIG. 3a) that couples to the low compliant section 205 and the high compliant section 201. Other embodiments of the connector are also contemplated. For example, the high compliant section 201 may be coupled to the low compliant section 205 through a sleeve 303 as seen FIG. 3b. The high compliant section 201 and low compliant section 205 may be coupled to the connector 301 and/or sleeve 303 through a friction fit, adhesive, etc. In some embodiments, the transition section 203 (e.g., the sleeve 303) may itself be flexible to add flexibility to the aspiration tubing in addition to the flexibility provided by the high compliant section 201. In some embodiments, the high compliant section 201 or the low compliant section 205 may fit around an end of the other section. As seen in FIG. 3c, the low compliant tubing 205 may fit over the high compliant tubing 201 and be coupled to the high complaint tubing 201 through a friction fit, adhesive, etc.

Figure 4:
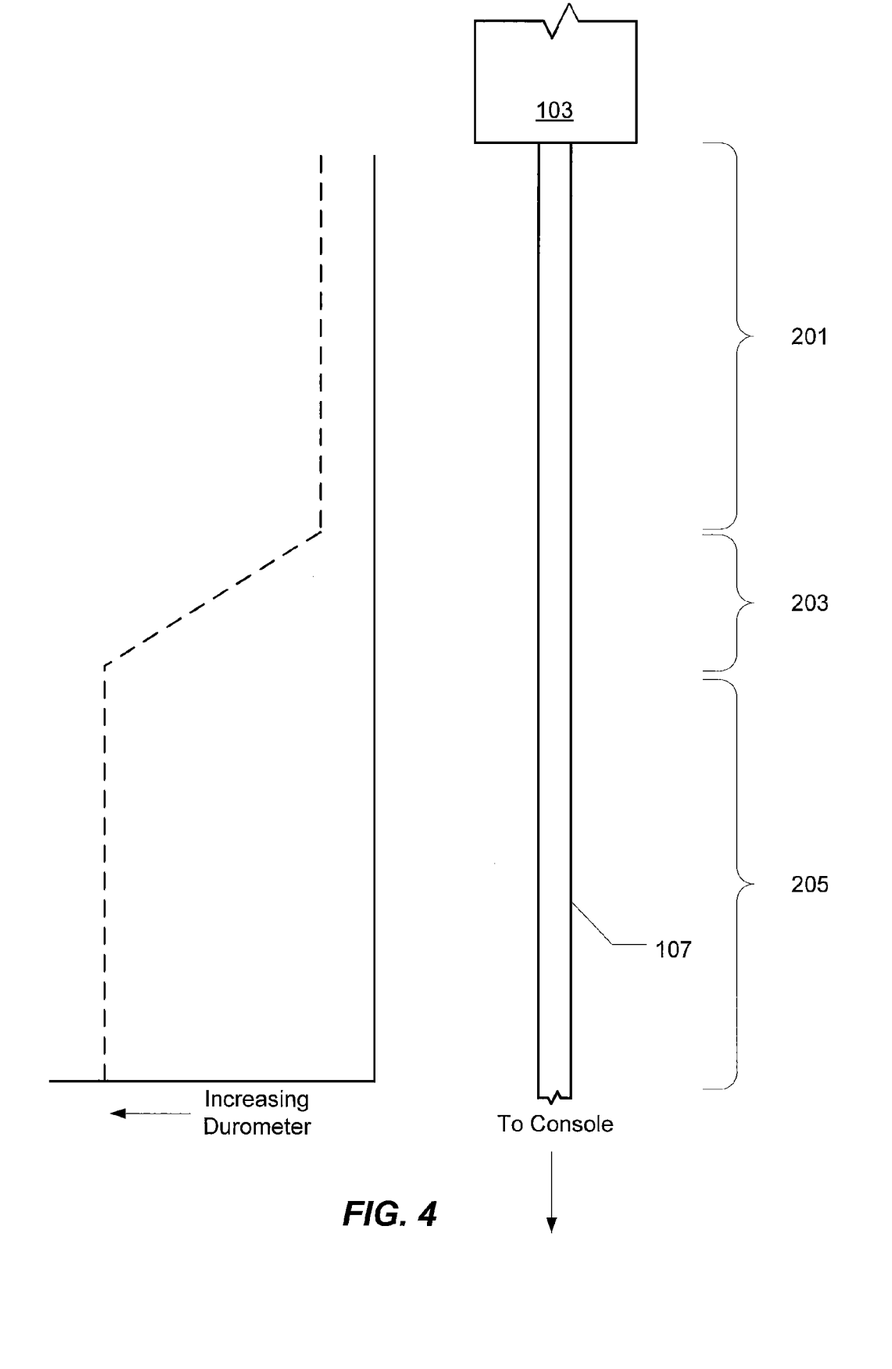
FIG. 4 illustrates a transition section including continuous section of tubing with an accompanying durometer diagram, according to an embodiment.
Figure 5A:
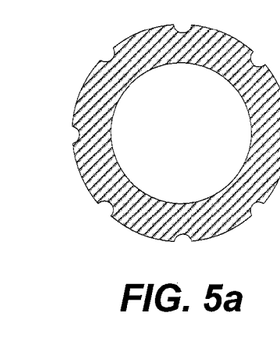
FIGS. 5a-e illustrate cross section geometries for various embodiments of the high compliant section.
Figure 5B:
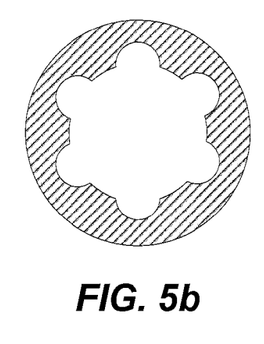
Figure 5C:
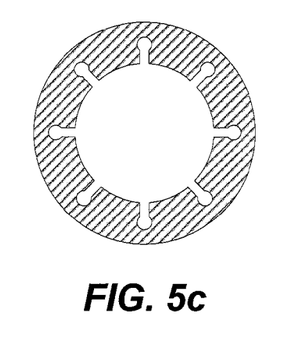
Figure 5D:
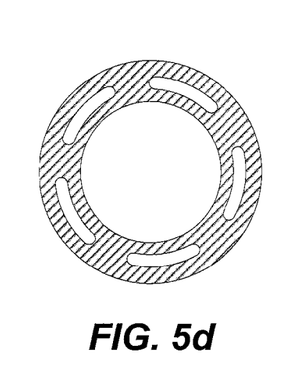
Figure 5E:
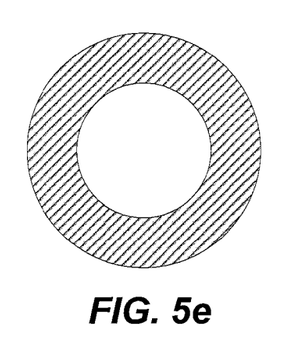
Figure 6A:
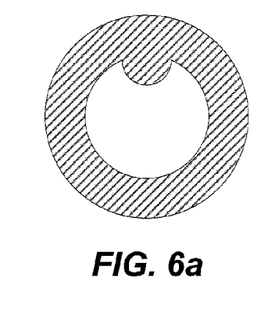
FIGS. 6a-f illustrate cross section geometries for various embodiments of the low compliant section.
Figure 6B:
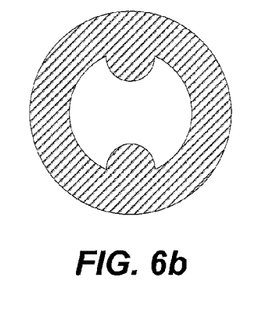
Figure 6C:
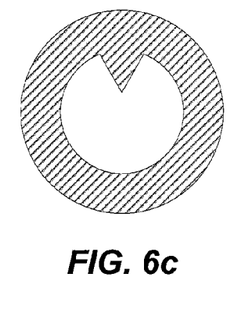
Figure 6D:
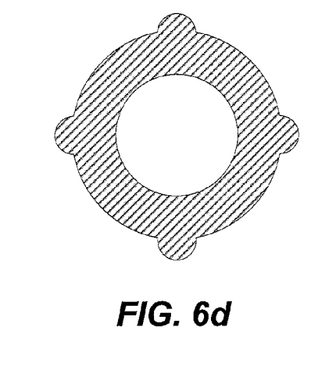
Figure 6E:
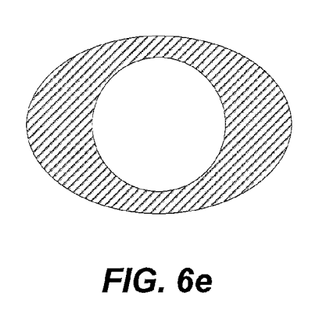
Figure 6F:
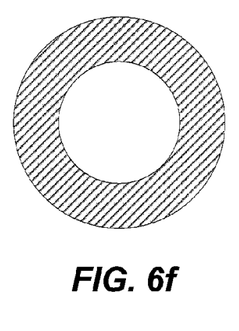

In some embodiments, the transition section 203 may include a section of tubing that is continuous with the high compliant section 201 and the low compliant section 205. For example, as seen in FIG. 4, the transition section 203 may be a section of tubing that has a low durometer at the high compliant section 201 and gradually increases in durometer down the length of the transition section 203. In some embodiments, the high compliant section 201 may be very short compared to the transition section 203 such that most of the tubing leading up to the low compliant section 205 includes a gradually increasing durometer up to the low compliant section 205 at which point the durometer may become constant. In some embodiments, the transition section 203 may be a section of tubing that has a geometry similar to the high compliant section geometry near the high compliant section 201 and gradually changes geometry down the length of the transition section 203 (until the geometry matches the low compliant section geometry where the transition section 203 meets the low compliant section 205). In some embodiments, the high compliant section 201 may be very short compared to the transition section 203 such that most of the tubing leading up to the low compliant section 205 includes a gradually changing geometry up to the low compliant section 205 (e.g., the wall thickness of the tubing may gradually increase along the tubing up to the low compliant section at which point the wall thickness may remain constant for the rest of the tubing).

In some embodiments, the tubing may be extruded through an extrusion mold that is configured to change configurations (e.g., with moving mold components) during the extrusion process (e.g., change configurations between a mold configured for a geometry of the high compliant section 201 to a mold configured for the geometry of the low compliant section 205). In some embodiments, material provided to the extrusion mold may be varied according to the tubing section being extruded. For example, a low durometer material may be supplied to the extrusion mold during molding of the high compliant section 201 and gradually the material provided to the extrusion mold may be changed to a higher durometer material for the low compliant section 205. During the change, a mixture of materials may be provided to the extrusion mold (which may result in the formation of the transition section 203).

In some embodiments, aspiration tubing 107 may be made as a continuous extrusion. For instance, high compliant section 201 may be extruded from one material (for instance a certain polymer). As the extrusion of high compliant section 201 ends and the extrusion of the transition section 203 begins, a transition from the first material to a second material may occur within the feed system of the extruder. As the extrusion of transition section 203 ends and the extrusion of low compliant section 205 begins, a transition from the second material to a third material can occur. Thus, by using chemically and mechanically compatible materials before and after material transitions, aspiration tubing 107 with sections of differing hardness may be created according to embodiments.

Different (or the same) materials may be fed to the extruder for aspiration tube 107 during various phases of the extrusion. In some embodiments, the sections of aspiration tubing 107 may be formed by extruding a common material, but injecting various hardeners (or concentrations thereof) into the common material during differing phases of the extrusion. Sections of differing hardness may be created from a common material via post processing of such portions in some embodiments. For instance, sections of the aspiration tubing 107 may be post-processed chemically to soften the "as formed" material to a select hardness for high compliant section 201, transition section 203, and low compliant section 205.

In some embodiments, radiation may be used to harden sections of aspiration tubing 107 to a select hardness for high compliant section 201, transition section 203, and low compliant section 205. Certain portions, such as transition section 203, may be further exposed to radiation to further harden such portions to another select, and higher, hardness. More particularly, in some embodiments, aspiration tubing 107 may be coiled up and exposed to radiation to sterilize sections of the aspiration tubing 107. In exposing aspiration tubing 107 to radiation, transition section 203 may be pre-positioned for radiation exposure, while high compliant section 201 and low compliant section 205 may be pre-positioned to extend from coils of aspiration tubing 107. By selectively applying radiation to transition section 203, transition section 203 may be exposed to radiation, sterilized, and hardened while high compliant section 201 and low compliant section 205 may remain relatively unexposed and relatively un-hardened. In some embodiments, all of aspiration tubing 107 may be radiation sterilized with transition section 203 being exposed to radiation for longer durations than high compliant section 201 and low compliant section 205. In some embodiments, some (for instance, high compliant section 201 and low compliant section 205) or all of aspiration tubing 107 may be chemically sterilized (by, for instance, exposure to ethylene oxide (ETO) gas).

In various embodiments, materials for the aspiration tubing may include, for example, silicone rubber and PVC (polyvinyl chloride). Other materials are also contemplated. Possible durometers for the aspiration line may include a durometer approximately in a range of between 80 ShoreA to 100 ShoreA (e.g., 90 ShoreA) for the low compliant section 205 and a durometer approximately in a range of 50 ShoreA to 70 ShoreA (e.g., 60 ShoreA) for the high compliant section 201. Other durometers are also contemplated (e.g., approximately in a range of between 70 ShoreA to 90 ShoreA for the low compliant section 205 and a durometer approximately in a range of 40 ShoreA to 60 ShoreA for the high compliant section 201). In some embodiments, the durometer ranges for the low compliant section 205 and the high compliant section 201 may not overlap (e.g., the durometer for the low compliant section 205 may be measurably higher than the durometer for the high compliant section 201).

In some embodiments, the high compliant section 201 may have a length of approximately 1 to 2 inches. Other ranges of lengths are also contemplated (e.g., 0 to 1 inch, 1.5 to 4 inches, 2 to 10 inches, etc). In some embodiments, the low compliant section 205 may include the rest of the tubing leading up to the console 101 (which may be approximately in a range of 50 to 90 inches (e.g., 70 inches)). Other lengths of tubing are also contemplated. In some embodiments, the high compliant section 201 may be coupled directly to the handpiece 103 (e.g., through a friction fit with a connector on the handpiece 103) or coupled indirectly (e.g., through another section of tubing between the high compliant section 201 and the handpiece 103). Similarly, the low compliant section 205 may be coupled directly to the console 101 (e.g., through a friction fit with a connector on the console 101) or coupled indirectly (e.g., through another section of tubing between the low compliant section 205 and the console 101). In some embodiments, the aspiration tubing may include repeating patterns of high compliant section 201, transition section 203, and low compliant section 205. For example, a first segment of high compliant section 201, transition section 203, and low compliant section 205 may be followed by a second segment of high compliant section 201, transition section 203, and low compliant section 205 coupled to the low compliant section 205 (or high compliant section 201) of the first segment.

Figure 7A:
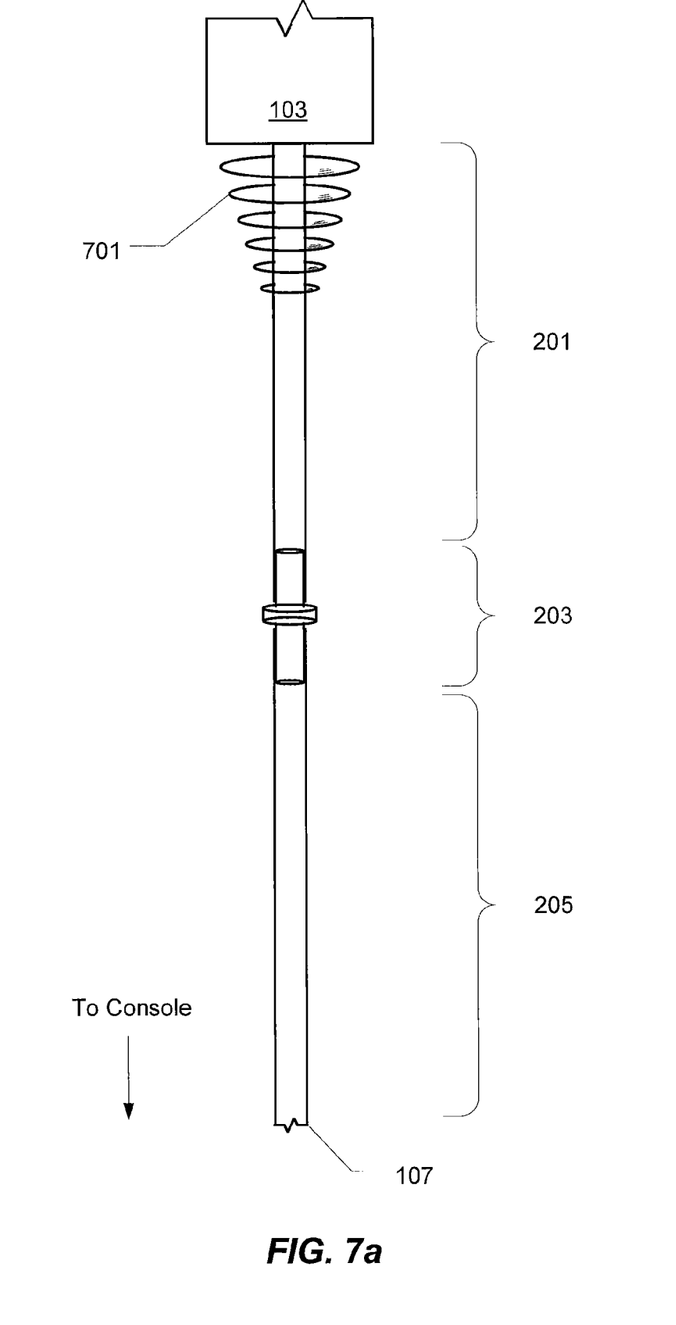
FIG. 7a-c illustrates various embodiments of stiffening configurations for the low compliant section.
Figure 7B:
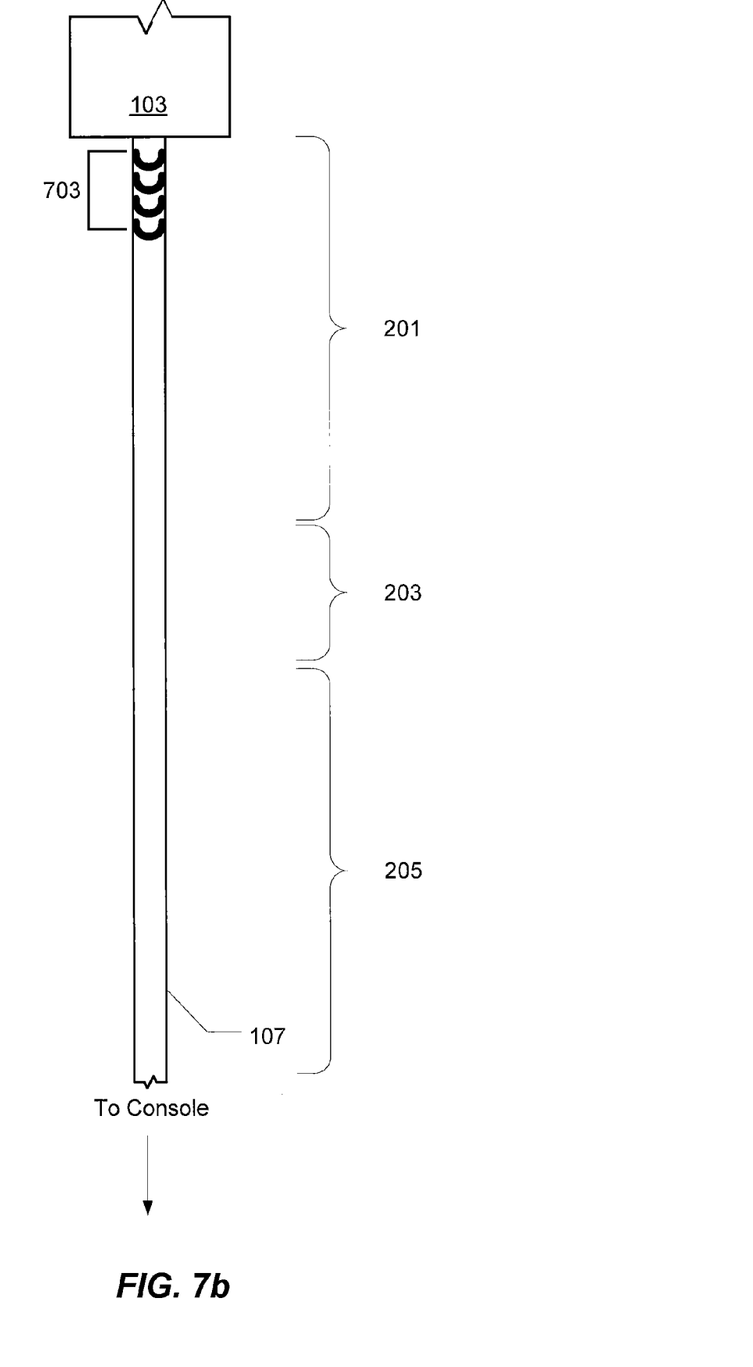
Figure 7C:
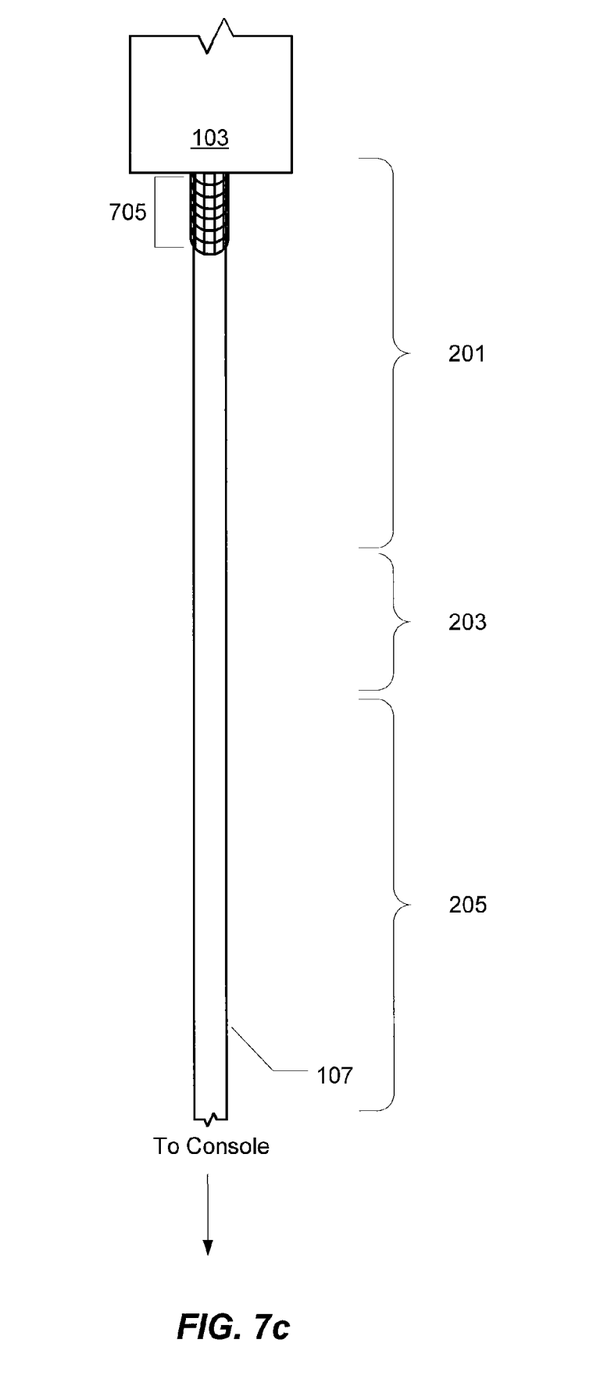

In some embodiments, the high compliant section 201 may include stiffening rings (e.g., rings 701 as seen in FIG. 7*a*), ribs (e.g., ribs 703 as seen in FIG. 7*b*), or a stiffening sleeve/sock (e.g., sleeve 705 as seen in FIG. 7*c*) to increase the stiffness of the high compliant section 201. In some embodiments, the sleeve 705 (and/or stiffening rings, ribs, etc.) may be made of a stiff material (e.g., a stiff plastic) which may fit tightly around the high compliant section 201. The sleeve 705 may have limited flex that may limit inflation of the high compliant section 201.

Figure 8:
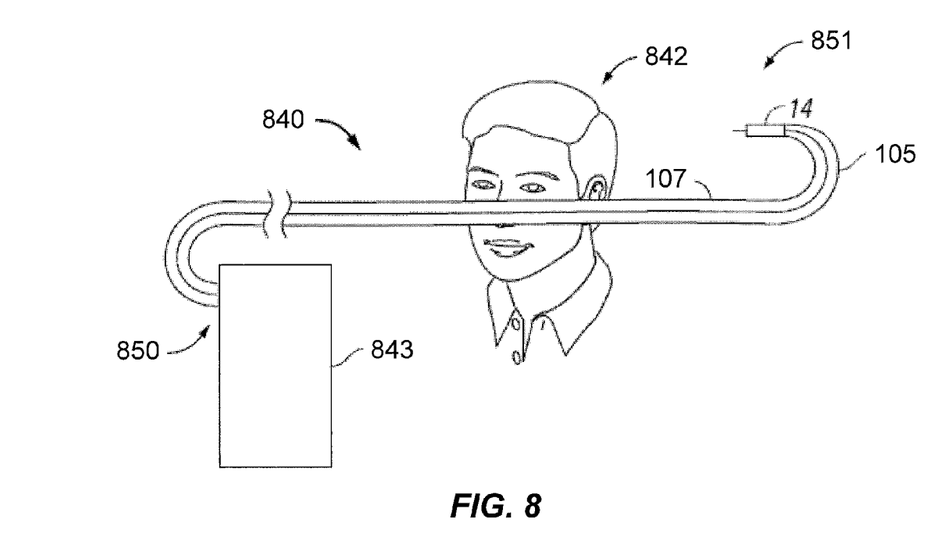
FIG. 8 illustrates a top plan view of one embodiment of a surgical system using twin bore ophthalmologic tubing.
Figure 9:
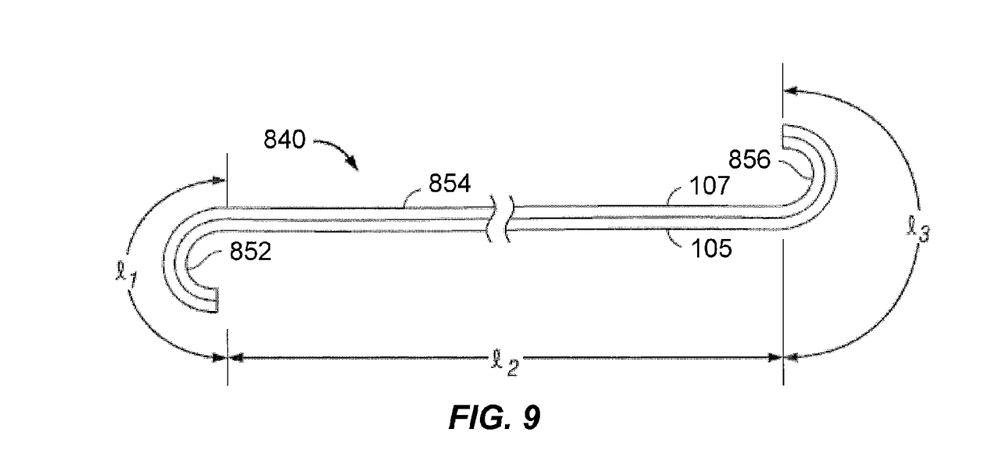
FIG. 9 illustrates a top plan view of one embodiment of a surgical system using twin bore ophthalmologic tubing.

With reference now to FIG. 8, one embodiment of twin bore ophthalmologic tubing 840 is illustrated. Twin bore ophthalmologic tubing 840 may be used with phacoemulsification, liquefaction, or other surgical systems which utilize irrigation/aspiration handpieces. Twin bore ophthalmologic tubing 840 may include irrigation tube 105, aspiration tube 107, proximal end 850, distal end 851, proximal end portion 852, mid portion 854, and distal end portion 856. Irrigation tube 105 and aspiration tube 107 may be joined to each other (or formed together via extrusion, injection molding, etc.) along substantially the length of twin bore ophthalmologic tubing 840. At proximal and distal ends 850 and 851, irrigation tube 105 and aspiration tube 107 may separate from each other to facilitate connecting twin bore ophthalmologic tubing 840 to certain handpieces 103 and fluidics modules (including the fluidics cassette) 843, control consoles, or the like for receiving and discharging liquid. Proximal and distal ends 850 and 851 may include adapters for connecting twin bore ophthalmologic tubing 840 to fluidics cassette(s) (which may be placed in fluidics modules 843), handpieces 103, etc. as desired or proximal and distal ends 850 and 851 may be dimensioned and shape to slidably engage, and seal against, ports on such devices. Proximal end portion 852 may have length l1, mid portion 854 can have length l2, and distal end portion 856 can have length l3. Lengths l1 and l3 can be about 6" to 12" in some embodiments and, more particularly, about 12" in some embodiments.

As surgical personnel operate to extract cataracts, perform cortical cleanup, etc. on patient 842, surgical personnel may desire to position themselves about patient 842 to observe patient 842, observe various anatomical features of patient 842, navigate handpiece 103, perform surgical techniques using handpiece 103, etc. In some situations, it may happen that surgical personnel may wish to navigate handpiece 103 into certain position(s) at which they desire twin bore ophthalmologic tubing 840 to bend through some arc. For instance, surgical personnel may desire to bring twin bore ophthalmologic tubing 840 across patient 842, turn distal end 851 though some arc (such as 180 degrees), and approach patient 842 with handpiece 103 from the side of patient 842 which is opposite fluidics module 843. In certain situations, surgical personnel may desire to bend proximal end 850 through some arc adjacent to fluidics module 843. Thus, in certain situations, surgical personnel may desire that twin bore ophthalmologic tubing 840 follow a relatively convoluted path as illustrated by FIG. 8.

In some embodiments, end portions 852 and 856 of twin bore ophthalmologic tubing 840 may be made from materials having relatively high compliance (e.g., with low hardness or a high compliance geometry). End portions 852 and 856 may therefore cause little or no reactions as surgical personnel navigate handpiece 103 about various surgical sites. Accordingly, end portions 852 and 856 may provide high navigability of handpiece 103. Other portions 854 of twin bore ophthalmologic tubing 840 may be made of materials having relatively low compliance (e.g., with high hardness or a low compliance geometry) thereby permitting no, or little, overall compliance of irrigation tube 105 and aspiration tube 107.

In some embodiments, end portions 852 and 856 may have a hardness of about 60 shore A to about 70 shore A while mid portion 854 can have a hardness of about 80 shore A to about 90 shore A. End portions 852 and 856 may be any length. However, in some embodiments, lengths l1 and l3 of end portions 852 and 856 may be about 6" to about 12" long. Mid portion 854 may be any length l2 although in some embodiments length l2 is about 6 feet.

Twin bore ophthalmologic tubing 840 may be made as a continuous extrusion in various embodiments. For instance, proximal end portion 852 can be extruded from one material (for instance a certain polymer). As the extrusion of proximal end portion 852 ends and the extrusion of mid portion 854 begins, a transition from the first material to a second material can occur within the feed system of the extruder. As the extrusion of mid portion 854 ends and the extrusion of distal end portion begins, a transition from the second material to a third material can occur. Thus, by using chemically and mechanically compatible materials before and after material transitions, twin bore ophthalmologic tubing 840 with portions 852, 854, and 856 of differing hardness may be created according to embodiments.

Different (or the same) materials may be fed to the extruder for irrigation tube 105 and/or for aspiration tube 107 during various phases of the extrusion (e.g., for separate tubing and/or twin bore ophthalmologic tubing 840). Thus, tubing may be created in which corresponding portions of irrigation tube 105 and/or aspiration tube 107 have differing or about the same hardness. In some embodiments, portions 852, 854, and 856 can be formed by extruding a common material, but injecting various hardeners (or concentrations thereof) into the common material during differing phases of the extrusion. Portions 852, 854, and 856 of differing hardness may be created from a common material via post processing of such portions in some embodiments. For instance, twin bore ophthalmologic tubing 840 may be post-processed chemically to soften the "as formed" material to a select hardness for end portions 852 and 856.

In some embodiments, radiation may be used to harden overall twin bore ophthalmologic tubing 840 to a select hardness for end portions 852 and 856. Certain portions, such as mid portion 854, may be further exposed to radiation to further harden such portions 854 to another select, and higher, hardness. More particularly, in some embodiments, twin bore ophthalmologic tubing 840 may be coiled up and exposed to radiation to sterilize twin bore ophthalmologic tubing 840. In exposing twin bore ophthalmologic tubing 840 to radiation, mid portions 854 may be pre-positioned for radiation exposure, while end portions 852 and 856 may be pre-positioned to extend from coils of twin bore ophthalmologic tubing 840. By selectively applying radiation to mid portions 854, mid portions 854 may be exposed to radiation, sterilized, and hardened while end portions 852 and 856 may remain relatively unexposed and relatively un-hardened. In some embodiments, all of twin bore ophthalmologic tubing 840 may be radiation sterilized with mid portions 854 being exposed to radiation for longer durations than end portions 852 and 856. In some embodiments, some (for instance, end portions 852 and 856) or all of twin bore ophthalmologic tubing 840 may be chemically sterilized (by, for instance, exposure to ethylene oxide (ETO) gas).

Embodiments provide twin bore ophthalmologic tubing with low compliance and low resistance to movement (even when connected to surgical handpieces and fluidics modules). Embodiments provide twin bore ophthalmologic tubing with rapid vacuum rise times in the aspiration line. Twin bore ophthalmologic tubing of embodiments are provided which allow compliance, navigability, and vacuum characteristics to be controlled by selecting hardness levels for various portions of the twin bore ophthalmologic tubing. Thus, twin bore ophthalmologic tubing of embodiments may increase the speed, efficiency, and accuracy of ophthalmologic procedures such as phacoemulsification, liquefaction, etc.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. An aspiration tubing, comprising:
   a high compliant section;
   a low compliant section having a different geometry than the high compliant section, wherein the different geometry gives the low compliant section a lower compliance than the high compliant section;
   a transition section coupling the high compliant section to the low compliant section such that fluid can travel through the transition section from the high compliant section and into the low compliant section;
   wherein the transition section comprises a length of tubing that is continuous with the high compliant section and the low compliant section;
   wherein an end of the transition section adjacent the high compliant section matches the geometry of the high compliant section and wherein an opposing end of the transition section that is adjacent the low compliant section matches the geometry of the low compliant section;
   wherein the transition section gradually changes geometry along the length of the transition section between matching the end adjacent the high compliant section and matching the opposing end adjacent the low compliant section;
   wherein the high compliant section is configured to couple to a handpiece; and
   wherein the low compliant section is configured to couple to a surgical console.

2. The aspiration tubing of claim 1,
   wherein the handpiece is an ophthalmic handpiece; and
   wherein surgical console is an ophthalmic surgical console.

3. The aspiration tubing of claim 1, wherein the high compliant section has a lower durometer than the low compliant section and wherein a durometer of the transition section gradually changes over the length of the transition section between matching the high compliant section and matching the low compliant section.

4. The aspiration tubing of claim 1, wherein the high compliant section further comprises at least one of ribs, rings, a spine, a sleeve, or a sock to decrease compliance of the high compliant section.

5. The aspiration tubing of claim 1, wherein the high compliant section has a durometer approximately in a range of 50 ShoreA to 70 ShoreA.

6. The aspiration tubing of claim 1, wherein the low compliant section has a durometer approximately in a range of 80 ShoreA to 100 ShoreA.

7. The aspiration tubing of claim 1, wherein the high compliant section has a length approximately in a range of 1 to 2 inches.

8. The aspiration tubing of claim 1, wherein the low compliant section has a length approximately in a range of 50 to 90 inches.

9. The aspiration tubing of claim 1, wherein a geometry of the high compliant section has a higher compliance than the geometry of the low compliant section and wherein an internal geometry of the transition section gradually changes over the length of the transition section between matching the high compliant section and matching the low compliant section.

10. A system, comprising:
    an ophthalmic surgical console;
    a handpiece coupled to the surgical console by an aspiration tubing and an irrigation tubing;
    wherein the aspiration tubing, comprises:
       a high compliant section configured to couple to the ophthalmic handpiece;
       a low compliant section configured to couple to the ophthalmic surgical console, wherein the low compliant section has a different geometry than the high compliant section, wherein the different geometry gives the low compliant section a lower compliance than the high compliant section; and
       a transition section coupling the high compliant section to the low compliant section such that fluid can travel through the transition section from the high compliant section and into the low compliant section;
    wherein the transition section comprises a length of tubing that is continuous with the high compliant section and the low compliant section;
    wherein an end of the transition section adjacent the high compliant section matches the geometry of the high compliant section and wherein an opposing end of the transition section that is adjacent the low compliant section matches the geometry of the low compliant section;
    wherein the transition section gradually changes geometry along the length of the transition section between matching the end adjacent the high compliant section and matching the opposing end adjacent the low compliant section.

11. The system of claim 10, wherein the high compliant section has a lower durometer than the low compliant section and wherein a durometer of the transition section gradually changes over the length of the transition section between matching the high compliant section and matching the low compliant section.

12. The system of claim 10, wherein the high compliant section of the aspiration tubing further comprises at least one of ribs, rings, a spine, a sleeve, or a sock to decrease compliance of the high compliant section.

13. The system of claim 10, wherein the high compliant section of the aspiration tubing has a durometer approximately in a range of 50 ShoreA to 70 ShoreA.

14. The system of claim 10, wherein the low compliant section of the aspiration tubing has a durometer approximately in 80 ShoreA to 100 ShoreA.

15. The system of claim 10, wherein the high compliant section of the aspiration tubing has a length approximately in a range of 1 to 2 inches.

16. The system of claim 10, wherein the low compliant section of the aspiration tubing has a length approximately in a range of 50 to 90 inches.

17. The system of claim 10, wherein a geometry of the high compliant section has a higher compliance than the geometry of the low compliant section and wherein an internal geometry of the transition section gradually changes over the length of the transition section between matching the high compliant section and matching the low compliant section.

* * * * *